United States Patent [19]

Perten

[11] Patent Number: 4,563,581
[45] Date of Patent: Jan. 7, 1986

[54] ARRANGEMENT IN INFRARED ANALYZERS

[76] Inventor: Peter Perten, An der Barsbek 33 B, D-2000 Barsbüttel, Fed. Rep. of Germany

[21] Appl. No.: 626,108

[22] Filed: Jun. 29, 1984

[30] Foreign Application Priority Data

Jul. 4, 1983 [SE] Sweden ............................. 8303817

[51] Int. Cl.⁴ ...................... G01N 21/35; G01N 21/55
[52] U.S. Cl. .................................... 250/338; 250/341; 250/359.1; 356/36; 356/445
[58] Field of Search ...................... 250/341, 359.1, 343, 250/338, 576, 358.1, 339; 356/445, 446, 448, 38, 36

[56] References Cited

U.S. PATENT DOCUMENTS

| | | | |
|---|---|---|---|
| 3,263,801 | 8/1966 | Dudte | 198/213 |
| 3,328,587 | 6/1967 | Brown et al. | 250/358.1 |
| 4,040,747 | 8/1977 | Webster | 250/339 |
| 4,180,331 | 12/1979 | Lundstrom | 356/445 |
| 4,400,086 | 8/1983 | Webster | 250/576 |
| 4,479,055 | 10/1984 | Perten | 250/343 |

FOREIGN PATENT DOCUMENTS 0069929 1/1983 European Pat. Off. .

Primary Examiner—Carolyn E. Fields
Attorney, Agent, or Firm—Fleit, Jacobson, Cohn & Price

[57] ABSTRACT

The invention relates to an arrangement in an infrared analyzer for determining the proportion of a given substance or substances in a powderous material, such as flour. When making an analysis, the infrared analyzer irradiates the material with infrared light and detects light reflected from the material through a window in the wall of a conduit, in which the material is passed in a direction substantially parallel with the window. During the analysis, the material is held stationary, and compacted in the conduit. The conduit has arranged therein a feed screw having a controllable drive-means in a material-infeed end, and extends horizontally or slopes upwardly from the aforementioned infeed end. A control means steers the drive means and the analyzer cyclically in a manner such that during a first time interval the drive means is activated and the analyzer inactivated, and that during a second time period the analyzer is activated and the drive means inactivated.

9 Claims, 4 Drawing Figures

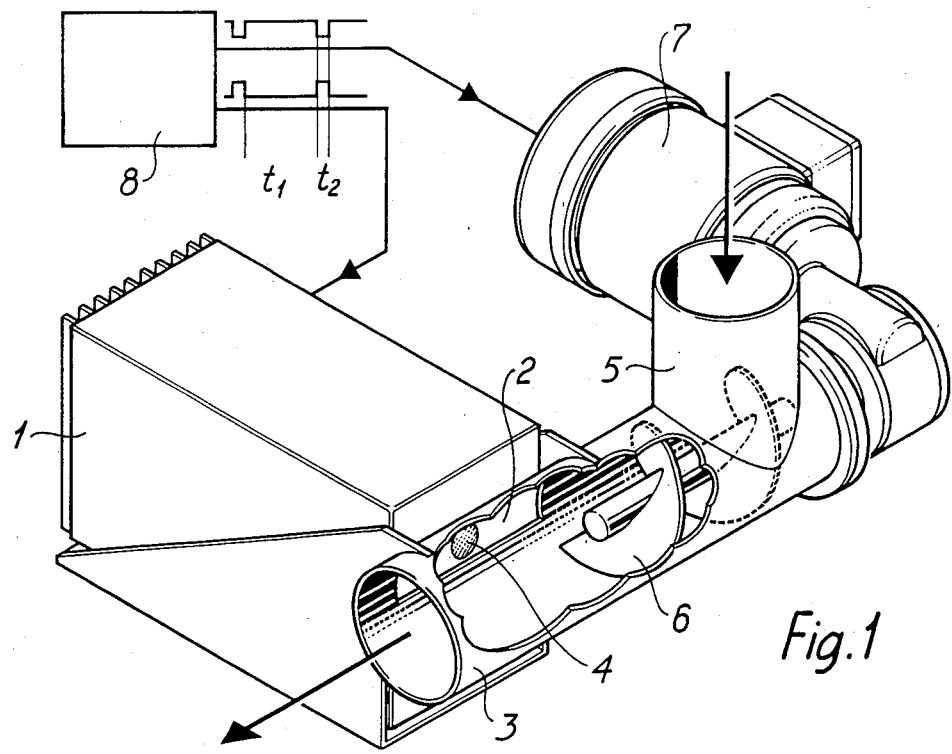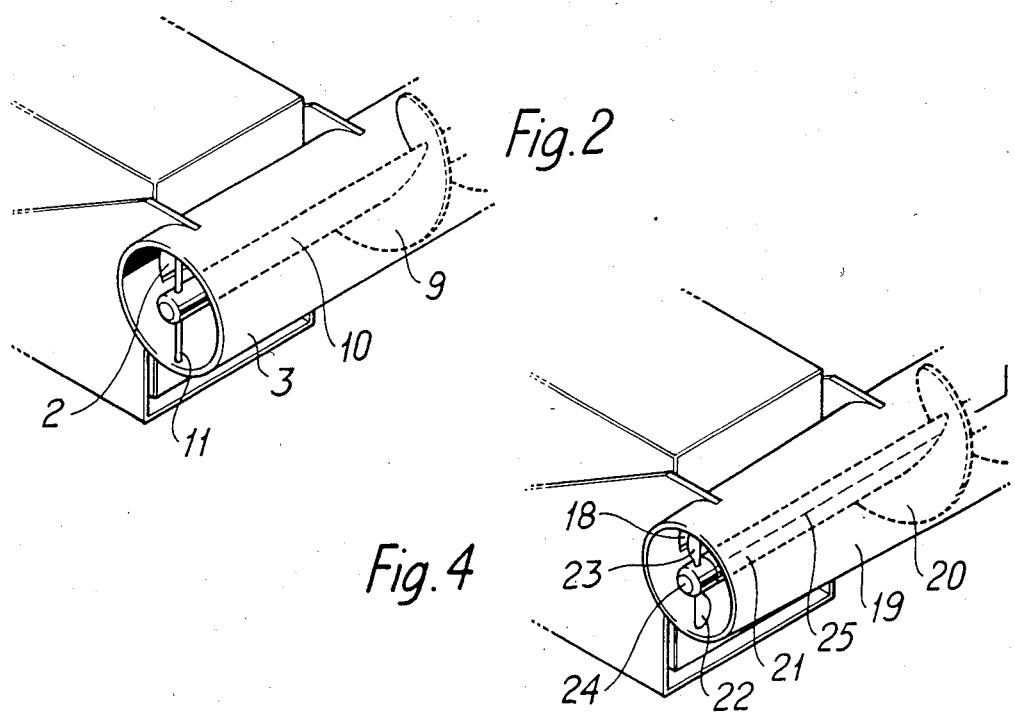

ARRANGEMENT IN INFRARED ANALYZERS

The invention relates to an arrangement in an infrared analyzer for determining the proportion of a given substance or substances in a powderous material, such as flour, in which during an analysis the infrared analyzer irradiates the material with infrared light and detects light reflected from the material through a window in the wall of a conduit in the form of a tube, through which the material is passed in a direction which is substantially parallel with the window, and is compacted in said conduit.

In particular the invention relates to an improvement of an arrangement described in Swedish Patent Application No. 8101655-2. This arrangement is intended for an infrared analyzer designed to analyze a powderous material, such as flour, to determine the proportion of a given substance or substances in the material, in which assay the infrared analyzer is caused to irradiate the material with infrared light and to detect light reflected from the material through a window in the wall in a conduit in which the material moves in a direction substantially parallel with the window, and during which analysis the material is compacted in said conduit.

There is an expressed desire in the art to be able to assay continuously flour which is advanced in a flour conveyor. In the Swedish Patent Application No. 8101655-2 there is described one embodiment of such an arrangement in which, for analysis purposes, the flour is fed vertically downwards through a shunt conduit which extends parallel with a flour gravity-shaft. The wall of the shunt conduit has a window arranged therein, and the infrared analyzer is placed adjacent the window. Downstream of the window there is arranged in the shunt conduit a valve which is closed just prior to making an assay, so that the flour piles up and becomes compacted in front of the window. Upon completion of the assay, the valve is re-opened, to allow the flour to continue through the conduit. This arrangement has not always functioned satisfactorily when subjected to continuous assaying operations, since the flour tends to pack so tightly in the vicinity of the valve, when it is closed, that it is sometimes unable to continue the flow through the conduit when the valve is re-opened. Consequently, the same flour plug is assayed repeatedly, until the plug has finally loosened and dispersed. As a result hereof, it has been necessary to provide some kind of means for mechanically advancing the flour between consecutive analyses.

One functionally satisfactory means herefor is obtained with the arrangement according to the invention which is characterized in that the conduit is provided with a feed screw having a controllable drive means arranged in a material-infeed end thereof and extends horizontally or slopes upwardly from said infeed end; and in that a control means is arranged to cyclically control the feed-screw drive means and the infrared analyzer, so that during a first time period the drive means is activated and the infrared analyzer is inactivated, and during a second time period the infrared analyzer is activated and the drive means inactivated.

Further characterizing features of the invention are set forth in the sub-claims.

The invention will now be described in more detail with reference to the accompanying drawing, in which FIG. 1 is a schematic side view, partially cut away, of a first embodiment of an arrangement according to the invention;

FIG. 2 is a partial schematic view in perspective of a second embodiment according to the invention;

FIG. 4 is a partial view in perspective of a fourth embodiment of the arrangement according to the invention.

Figure 3:
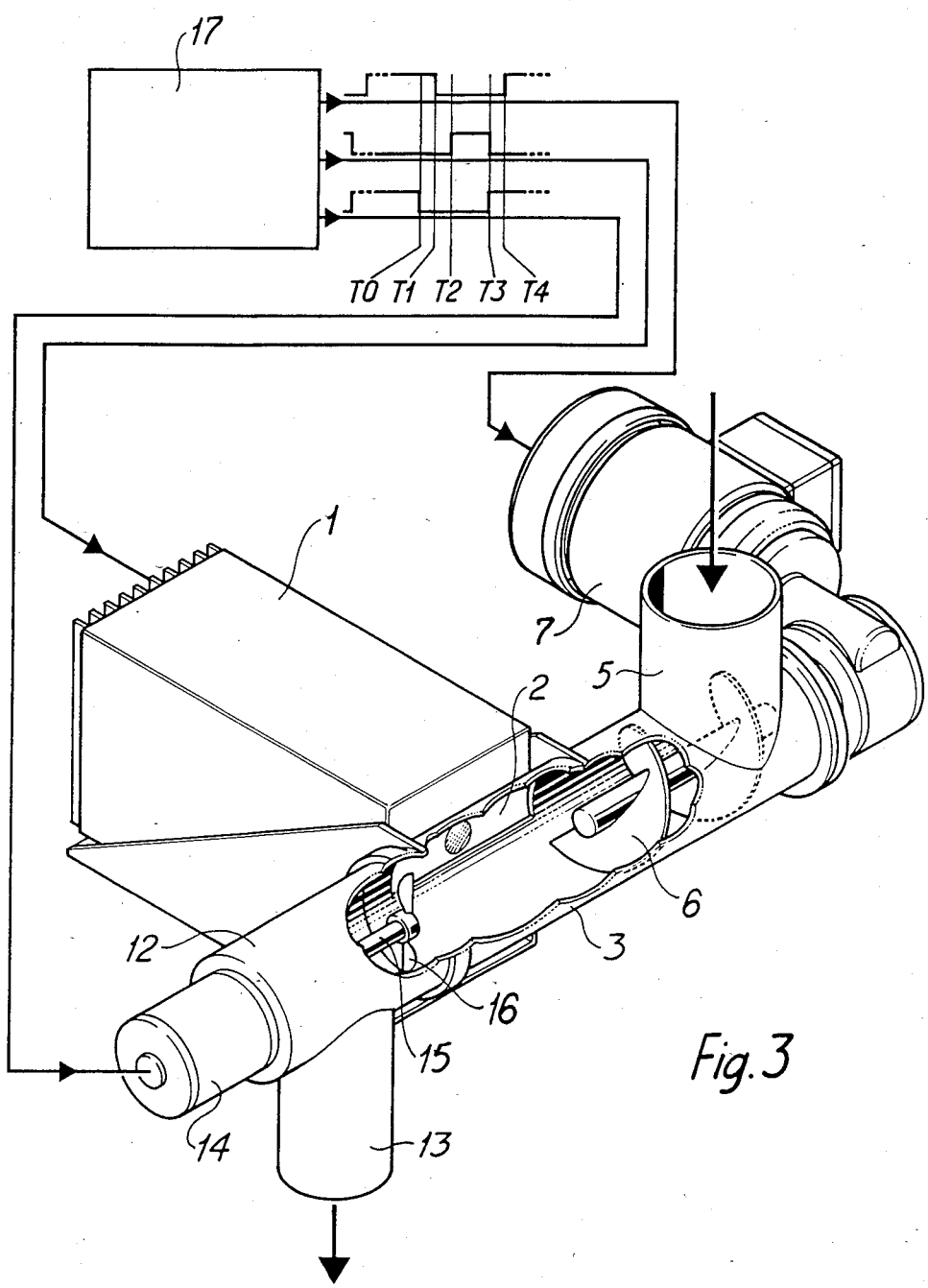
FIG. 3 is a partial view of a third embodiment of the arrangement according to the invention.

FIG. 1 illustrates an infrared analyzer 1 of the kind in which when carrying out an assay, the material to be analyzed is irradiated with infrared light and the light through a window 2 in the wall of a conduit 3 is detected and measured. The area over which the analyzer works is illustrated at 4. The internal surfaces of the conduit 3 are preferably smooth, so that flour does not fasten to and be held by said surfaces. Flour is fed into the conduit through a branch-pipe 5 connected thereto. The branch-pipe 5 is preferably vertical, and the flour is fed therethrough gravitationally. Mounted in the conduit 3 is a feed screw 6, which is positioned so as to extend through the join of the branch pipe 5, practically to the window 2. The screw 6 is driven by a controllable motor 7. A control means 8 is arranged to steer the motor 7 and the analyzer 1 so that the motor is activated to drive the feed screw 6 and the analyzer 1 is in its non-activated state during a first time period t1, and to stop the motor 7, so that the screw is stationary, and activate the analyzer 1 during a second time period t2. The time periods t1 and t2 may be of any desired duration, although the time period t1 is preferably of longer duration than the time period t2. In order to ensure that the flour located in front of the window 2 is quite stationary when making the assay, the control means can also be designed to delay activation of the analyzer 1 in the second time period for a given short period of time, subsequent to stopping the motor 7.

The conduit 3 may either extend horizontally or may slope upwards from the infeed end (not shown), so that when making the assay the flour is well packed in front of the window, within the area 4. The outfeed end of the conduit 3 is preferably located further to the left than shown in the drawing, and either discharges into a flour feed conduit, such as a flour shaft, or is also connected to a pipeelbow or a pipe connection fitted with a branch pipe, such that the flour passing through the conduit 3 is fed to a substantially vertical conduit or chute, and falls therethrough gravitationally.

Powderous material, such as flour, readily becomes packed in the conduit 3, and a great deal of power is required from the motor 7 to renew rotation of the feed screw 6 after a stationary period. FIG. 2 illustrates an arrangement which facilitates such renewed rotation of the screw 9. In this arrangement the shaft 10 of the screw is extended beyond the window 2, and a pin 11, which is slightly shorter than the diameter of the conduit 3, is inserted through a hole traversing the shaft 10 adjacent the end thereof. The pin 11 essentially has two functions. Firstly, when restarting the feed screw 9, the pin loosens up the flour plug located at the outlet end, so as to facilitate renewed rotation of the feed screw 9. Secondly, the pin assists in maintaining the flour located in the conduit 3 in front of the window 2 in a compacted state, when the feed screw 9 is stopped so that an analysis can be made.

FIG. 3 illustrates a third embodiment of the arrangement according to the invention. The Figure illustrates the same analyzer arrangment 1 as that illustrated in FIG. 1, i.e. an analyzer comprising the conduit 3, the feed screw 6 and the motor 7. Arranged at the outfeed end of the conduit 3 is a branch-pipe coupling 12, with the branch pipe 13 thereof extending downwardly. An additional controllable motor 14 is arranged at one end of the straight part of the coupling 12, with the shaft 15 of the motor extending parallel with the long axis of said straight coupling-part. Seated on the free end of the shaft 15 is a propeller 16. The propeller 16 may be replaced with a pin similar to the pin 11, although a propeller is more effective. The use of a flour screw is also conceivable.

A control means 17 is designed to steer the motor 14, the analyzer 1 and the motor 7 in accordance with the time diagram illustrated by the output conductors of the means 17. The means 17 is so designed that at the end of a time period in which the analyzer 1 is inactivated and both motors are activated, i.e. running, the motor 14 is caused to stop at time T0, shortly before the time T1 at which the motor 7 is caused to stop. This results in the flour being packed harder in front of the window, for analysis purposes. The analyzer 1 is controlled so as to be activated at time T2, shortly after the motor 7 is deactivated. This enables the propeller 14 to loosen the flour plug at the outlet end of the conduit 3 over a short period prior to time T4, at which point in time the motor is re-started, therewith facilitating said re-starting of the motor. This control sequence is repeated cyclically. When making an analysis, it is essential that the flour is well compacted in front of the window. FIG. 4 illustrates an embodiment in which the window 18 is located in a narrowing conduit 19, with the diameter of said conduit decreasing from the infeed end thereof. As with the FIG. 2 embodiment, the shaft 21 of the feed screw 20 is extended beyond the window 18. Although the end of shaft 21 may be provided with the same pin arrangement 11 as that of the FIG. 2 embodiment, the shaft is shown in FIG. 4 to be provided with controllable, adjustable propeller blades 22 and 23. The propeller blades are seated on an adjustable setting means 24 mounted on one end of the shaft 21, and are controlled via a conductor 25 passing centrally through the shaft 21.

Setting of the propeller blades 22 and 23 is controlled analogously with the control of the motor 14 of the FIG. 3 embodiment, such that the blades are set to a position which assists in the forward feed of the flour in the conduit, when the motor 7 is started up. Shortly before the motor 7 is brought to a stop, the setting of the propeller blades 22,23 is changed to one which counteracts the forward feed of flour at the outfeed end of the conduit, so as to further compact the flour subjected to said analysis. Upon completion of the analysis, the propeller blades are again adjusted to a flour forward-feed setting, shortly before the motor 7 is activated and started up.

It will be understood that many modifications can be made within the scope of the following claims. It will be noted that the invention is not only suited for advancing flour, but can be used for advancing any powderous material whatsoever.

I claim:

1. An arrangement in an infrared analyzer for determining the proportion of a given substance or substances in a powderous material, in which during an analysis the infrared analyzer irradiates the material with infrared light and detects light reflected from the material through a window in the wall of a conduit in the form of a tube through which the material is passed in a direction which is substantially parallel with the window, and is compacted in said conduit, the conduit is provided with a feed screw having a controllable drive means arranged in a material-infeed end thereof and extends horizontally or slopes upwardly from said infeed end; and a control means is arranged to cyclically control the feed-screw drive means and the infrared analyzer, such that during a first time period the drive means is activated and the infrared analyzer is inactivated, and during a second time period the infrared analyzer is activated and the drive means inactivated.

2. An arrangement according to claim 1, in which the conduit narrows at the window region thereof.

3. An arrangement according to claim 1 in which the control means is arranged to activate the analyzer for a period of time which is short in relation to the total time cycle, after said control means has inactivated the feed-screw drive means.

4. An arrangement in a infrared analyzer for determining the proportion of a given substance to substances in a powderous material, in which during an analysis the infrared analyzer irradiates the material with infrared light and detects light reflected from the material through a window in the wall of a conduit in the form of a tube through which the material is passed in a direction which is substantially parallel with the window, and is compacted in said conduit, the conduit is provided with a feed screw having a controllable drive means arranged in a material-infeed and thereof and extends horizontally or slopes upwardly from said infeed end, a control means is arranged to cyclically control the feed-screw drive means and the infrared analyzer, such that during a first time period the drive means is activated and the infrared analyzer is inactivated, and during a second time period the infrared analyzer is activated and the drive means inactivated, and an agitating or stirring means is arranged in the outfeed end of the conduit.

5. An arrangement according to claim 4 in which the feed screw and the agitating or stirring means are seated on a shaft which is common thereto and are driven by the same drive means.

6. An arrangement according to claim 4 in which the agitating or stirring means has an individual drive means which is controlled by said control means.

7. An arrangement according to claim 6 in which the control means is arranged to control means for driving the agitating or stirring means in a manner such that in relation to a full time cycle said agitating or stirring means remains inactivated for a short period of time prior to the control means starting-up the feed-screw drive means, and such that said agitating or stirring means is activated for a short period of time prior to said control means starting-up the feed-screw drive means.

8. An arrangement according to claim 4, in which the agitating or stirring means comprises a propeller having blades whose settings are adjusted by means of a controllable setting means.

9. An arrangement according to claim 8, in which the control means is arranged to steer the setting means of the agitating or stirring means in a manner such as to set the blades in a position which counteracts the advance of said material through said conduit for a period of time which is short in relation to the total time cycle, prior to said control means inactivating the feed-screw drive means, and such as to set said blades in a material-advancing position for a period of time which is short relative to the total time cycle, prior to the control means activating said feed-screw drive means.

* * * * *